(12) United States Patent
Lopez et al.

(10) Patent No.: US 7,008,792 B2
(45) Date of Patent: Mar. 7, 2006

(54) METHOD OF MEASUREMENT OF NUCLEATED RED BLOOD CELLS

(75) Inventors: Lidice L. Lopez, Miami, FL (US); Carlos A. Perez, Miami, FL (US); Mark A. Wells, Davie, FL (US); Diana B. Careaga, Miami, FL (US); Ziling Huo, Miami, FL (US); Cheng Qian, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/048,086

(22) Filed: Feb. 1, 2005

(65) Prior Publication Data

US 2005/0176152 A1   Aug. 11, 2005

Related U.S. Application Data

(60) Provisional application No. 60/543,162, filed on Feb. 10, 2004.

(51) Int. Cl.
*G01N 31/00* (2006.01)
*G01N 33/48* (2006.01)

(52) U.S. Cl. ............... 436/10; 436/63; 436/164; 436/175; 435/2

(58) Field of Classification Search ............ 436/8, 436/10, 17, 63, 164, 174, 175; 435/2
See application file for complete search history.

(56) References Cited

U.S. PATENT DOCUMENTS

| | | |
|---|---|---|
| 2,656,508 A | 10/1953 | Coulter |
| 3,810,011 A | 5/1974 | Coulter et al. |
| 4,521,518 A | 6/1985 | Carter et al. |
| 4,528,274 A | 7/1985 | Carter et al. |
| 5,125,737 A | 6/1992 | Rodriguez et al. |
| 5,298,426 A | 3/1994 | Inami et al. |
| 5,559,037 A | 9/1996 | Kim et al. |
| 5,648,225 A | 7/1997 | Kim et al. |
| 5,763,280 A | 6/1998 | Li et al. |
| 5,834,315 A | 11/1998 | Riesgo et al. |
| 5,874,310 A | 2/1999 | Li et al. |
| 5,879,900 A | 3/1999 | Kim et al. |
| 5,882,934 A | 3/1999 | Li et al. |
| 5,917,584 A | 6/1999 | Li et al. |
| 5,935,857 A | 8/1999 | Riesgo et al. |
| 6,187,590 B1 * | 2/2001 | Kim et al. .......... 436/10 |
| 6,228,652 B1 * | 5/2001 | Rodriguez et al. ...... 436/63 |
| 6,410,330 B1 | 6/2002 | Li et al. |
| 6,472,215 B1 | 10/2002 | Huo et al. |
| 6,514,763 B1 | 2/2003 | Carver et al. |
| 6,573,102 B1 | 6/2003 | Li et al. |
| 6,653,063 B1 | 11/2003 | Carver et al. |
| 6,653,137 B1 | 11/2003 | Ryan |
| 6,723,563 B1 | 4/2004 | Ryan |
| 6,798,508 B1 | 9/2004 | Kramer |
| 2001/0046708 A1 | 11/2001 | Carver et al. |
| 2003/0104630 A1 | 6/2003 | Ryan |
| 2005/0074894 A1 * | 4/2005 | Li et al. ............. 436/63 |
| 2005/0079623 A1 * | 4/2005 | Ortiz et al. ........... 430/63 |

FOREIGN PATENT DOCUMENTS

EP   1044880 A2   5/2000

\* cited by examiner

*Primary Examiner*—Maureen M. Wallenhorst
(74) *Attorney, Agent, or Firm*—Cuspa Technology Law Associates; Mitchell E. Alter

(57) ABSTRACT

Methods are provided for measurement of nucleated red blood cells. The methods include exposing a blood cell sample to a reagent system to lyse mature red blood cells, subsequently analyzing nucleated red blood cells in a flow cell by axial light loss, low angle light scatter and DC impedance measurements, or two selected measurements thereof; and then differentiating nucleated red blood cells from other cell types by using measured signals and/or functions thereof.

26 Claims, 10 Drawing Sheets

METHOD OF MEASUREMENT OF NUCLEATED RED BLOOD CELLS

CROSS REFERENCE TO RELATED APPLICATION

This application claims the benefit under 35 USC 119 (e) of the provisional patent application Ser. No. 60/543,162, filed on Feb. 10, 2004, which is herein incorporated by reference in its entirety.

FIELD OF THE INVENTION

The present invention relates to a method for the measurement of nucleated red blood cells by optical and impedance measurements.

BACKGROUND OF THE INVENTION

Normal peripheral blood contains mature red blood cells which are free of nucleus. Nucleated red blood cells (NRBC), or erythroblasts, are immature red blood cells. They normally occur in the bone marrow but not in peripheral blood. However, in certain diseases such as anemia and leukemia, nucleated red blood cells also occur in peripheral blood. Therefore, it is of clinical importance to measure NRBC. Traditionally, differentiation and enumeration of nucleated red blood cells are performed manually. The process involves the smearing of a blood sample on a microscope slide and staining the slide, followed by manual visual analysis of the individual slide. The nucleated red blood cell concentration is reported as numbers of NRBC per 100 white blood cells (WBC). Usually, 200 white blood cells and the numbers of NRBC present in the same region on a blood smear are counted and the numbers are divided by 2 to express the NRBC concentration as the numbers of NRBC/100 WBC. This approach is extremely time-consuming as well as being subjective to the interpretation of the individual analyzing the slide.

In recent years, several fluorescence flow cytometry methods have been developed for differentiating nucleated red blood cells. These methods utilize nuclear specific staining techniques to distinguish nucleated red blood cells from other cell types because it is difficult to differentiate nucleated red blood cells only based on their electronic or optical properties.

U.S. Pat. No. 5,298,426 (to Inami et al.) discloses a fluorescence method for differentiating nucleated red blood cells. The method utilizes a two-step staining using a first fluid and a second fluid. Inami et al. teaches that the first fluid contains an erythroblast-staining dye that diffuses into nucleated red blood cells to specifically stain their nuclei, and then separating a group of nucleated red blood cells from other cell groups on a two-dimensional plot whereby the results of NRBC differentiation are computed.

U.S. Pat. No. 5,559,037 (to Kim et al.) discloses a method for flow cytometric analysis of nucleated red blood cells and leukocytes. The method comprises lysis of red blood cells and NRBC cytoplasm from a whole blood sample to expose the nucleated red blood cell nuclei to a vital nuclear stain and minimizing the permeation of the vital nuclear stain into the leukocytes and analyzing the sample by measuring fluorescence and two angles of light scatter. This method features a triple triggering method which blocks signals from debris (fluorescent and non-fluorescent) and identifies the signals which fall below the axial light loss (ALL) trigger but above the fluorescence trigger (FL3) as NRBCs. This method requires heating of the reagent to 42° C. in order to obtain the NRBC and leukocyte differentiations.

U.S. Pat. No. 5,648,225 (to Kim et al) discloses a method of using a multipurpose lysing reagent for subclassification of nucleated blood cells. The method comprises the steps of lysing a blood sample with the multipurpose lysing reagent which contains a nuclear stain, incubating the sample mixture at an elevated temperature, and determining the nucleated blood cells including NRBCs with an automated electro-optical hematology instrumentation.

U.S. Pat. No. 5,879,900 (to Kim et al) discloses a method of differentiating NRBCs, white blood cells (WBC), damaged white blood cells, and white blood cell subpopulations in a blood sample by flow cytometry. The method includes lysing a blood sample; staining nucleated red blood cells and any damaged white blood cells with a vital nuclear stain; analyzing the sample mixture by measuring fluorescence, axial light loss and light scatter signals from 3° to 10°; constructing a three-dimensional plot from the fluorescence and light scatter signals; and differentiating and enumerating WBC, NRBC, damaged WBC and a WBC subclass differential.

EP 1 004 880 A2 discloses reagents and a method for discrimination and counting of nucleated red blood cells. The method includes the steps of lysing red blood cells, staining white blood cells and nucleated red blood cells, assaying the sample by measuring at least one scattered light parameter, and at least one fluorescence parameter.

The above described methods enable differentiation and enumeration of nucleated red blood cells and leukocytes by combined fluorescence and light scatter measurements. However, fluorescence measurements are complex and expensive detection methods.

U.S. Pat. No. 5,874,310 (to Li et al) discloses a method for differentiation of nucleated red blood cells. The method includes lysing mature red blood cells and analyzing the sample in a flow cell by light scatter measurements to differentiate nucleated red blood cells from other cell types. The light scatter measurements are performed by using two low angle light scatter signals of less than 10°. The method further includes a concurrent differentiation of white blood cells using electronic and optical analyses, wherein the electronic analysis is a DC impedance measurement.

U.S. Pat. No. 5,917,584 (to Li et al) further discloses a method using two angles of light scatter measurements to differentiate nucleated red blood cells from other cell types, wherein the first light scatter signal is a low angle light scatter signal and the second light scatter signal is a medium angle or a right-angle light scatter signal.

U.S. Pat. No. 6,410,330 (to Li et al) also discloses a method for differentiation of nucleated red blood cells. The method includes the steps of lysing red blood cells of a blood sample with a lytic reagent, measuring nucleated blood cells by DC impedance measurement in a non-focused flow aperture, differentiating nucleated red blood cells from other cell types, and reporting nucleated red blood cells in the blood sample.

U.S. Pat. No. 6,472,215 (to Huo et al) teaches a method of differentiating nucleated red blood cells by lysing a first aliquot and a second aliquot of a blood sample separately with a first lysing reagent system and a second lysing reagent system, respectively; measuring the first sample mixture in a flow cell by DC impedance, radio frequency, and light scatter measurements; measuring cell distributions and counting remaining blood cells in the second sample mixture by DC impedance measurements in a non-focused flow aperture; analyzing blood cell distribution patterns obtained from measuring the first sample mixture and from measuring the second sample mixture respectively; and further performing a combined analysis to differentiate NRBCs from other cell types and determine numbers of NRBCs in the blood sample.

It is known that differentiation of nucleated red blood cells from other cell types, particularly white blood cells, is technically challenging because of the potential overlapping signals from other cell types, when measured by their size, and light scatter and fluorescence properties. The prior art detection systems and detection methods can be further improved in terms of cost, simplicity and efficiency of the measurement.

Based on foregoing, there still exist a need for a simple, less costly, yet reliable detection method and apparatus for differentiating and enumerating nucleated red blood cells.

SUMMARY OF THE INVENTION

In one embodiment, the present invention is directed to a method for differentiating nucleated red blood cells from other cell types in a blood cell sample. The method comprises the steps of exposing the blood cell sample to a reagent system to lyse mature red blood cells and to form a sample mixture; analyzing the sample mixture in a flow cell by measuring axial light loss and DC impedance signals; differentiating nucleated red blood cells from other cell types using signals consisting of the axial light loss and DC impedance signals; and reporting nucleated red blood cells in the blood cell sample. Furthermore, one or more functions of the axial light loss and DC impedance signals can be used for differentiating nucleated red blood cells from other cell types in the blood cell sample. Moreover, the method further comprises differentiating white blood cells into at least four subpopulations.

In another embodiment, the sample mixture is analyzed in a flow cell by measuring low angle light scatter and axial light loss signals, and the nucleated red blood cells are differentiated from other cell types by using the obtained low angle light scatter and axial light loss signals. The low angle light scatter signal is less than 10°, and preferably in a range from about 1° to about 7°. Furthermore, one or more functions of the low angle light scatter and axial light loss signals can be used for differentiating nucleated red blood cells from other cell types in the blood cell sample. Moreover, the method also comprises differentiating white blood cells into at least three subpopulations.

In a further embodiment, the sample mixture is analyzed in a flow cell by measuring DC impedance, low angle light scatter and axial light loss signals, and the nucleated red blood cells are differentiated from other cell types using the obtained DC impedance, low angle light scatter and axial light loss signals. Furthermore, one or more functions of the DC impedance, low angle light scatter and axial light loss signals can be used for differentiating nucleated red blood cells from other cell types. Moreover, the method further comprises differentiating white blood cell into at least four subpopulations.

In addition, the methods described above further include correction of white blood cell count from the interference of nucleated red blood cells by subtracting the nucleated red blood cells from a total nucleated cell count.

As will be better appreciated from the ensuing Detailed Description of Preferred Embodiments, the invention is particularly advantageous compared to the prior art in that it provides differentiation of nucleated red blood cells utilizing DC impedance, light scatter and axial light loss measurements without nuclear staining and the use of costly fluorescence detection methods. An additional feature of the present method is that it does not require heating for sample preparation and operates optimally at room temperature. The invention will be better understood from the ensuing description of preferred embodiments.

DETAILED DESCRIPTION OF THE INVENTION

In one embodiment, the present invention provides a method of differentiating nucleated red blood cells from other cell types using a combination of axial light loss and DC impedance measurements. The method comprises the steps of exposing a blood cell sample to a reagent system to lyse mature red blood cells; analyzing the sample in a flow cell by measuring axial light loss and DC impedance signals; differentiating nucleated red blood cells from other cell types using the axial light loss and the DC impedance signals; and reporting nucleated red blood cells in the blood cell sample.

The measurement of nucleated red blood cells is performed in a focused-flow flow cell using optical and impedance measurements. When a particle, such as a blood cell, passes through the aperture of a flow cell, it scatters the incident light from an illumination source causing light scatter to emit in all directions. The light scatter signals can be detected by a photo-detector at various angles relative to the incident light beam between 0° to 180°. It has been found that each cell population has different light scattering properties, either significant or minor, which can be utilized for differentiation of different cell populations. The light scatter signals detected in less than 10° from the incident light is commonly called low angle light scatter. The characteristics of low angle light scatter are affected by the size of a cell as well as the contents of a cell.

Axial light loss (ALL, also known as forward extinction) is generally the decrease in light energy due to a particle passing through a beam of incident light and being detected by a photo-detector. When the beam of incident light strikes a particle, the light is either scattered or absorbed, both of which remove energy from the incident light and the incident beam is attenuated. This attenuation is referred to as extinction. When viewed along the axis of the beam of incident light, it is referred to as axial light loss. Generally ALL signals are detected at an angle from about 0° to about 1° from the incident light. In a preferred embodiment of the present invention, ALL signals are collected in a circular area less than about 0.5° from the incident light axis. ALL signals are strongly influenced by the size of the cell.

Figure 10:
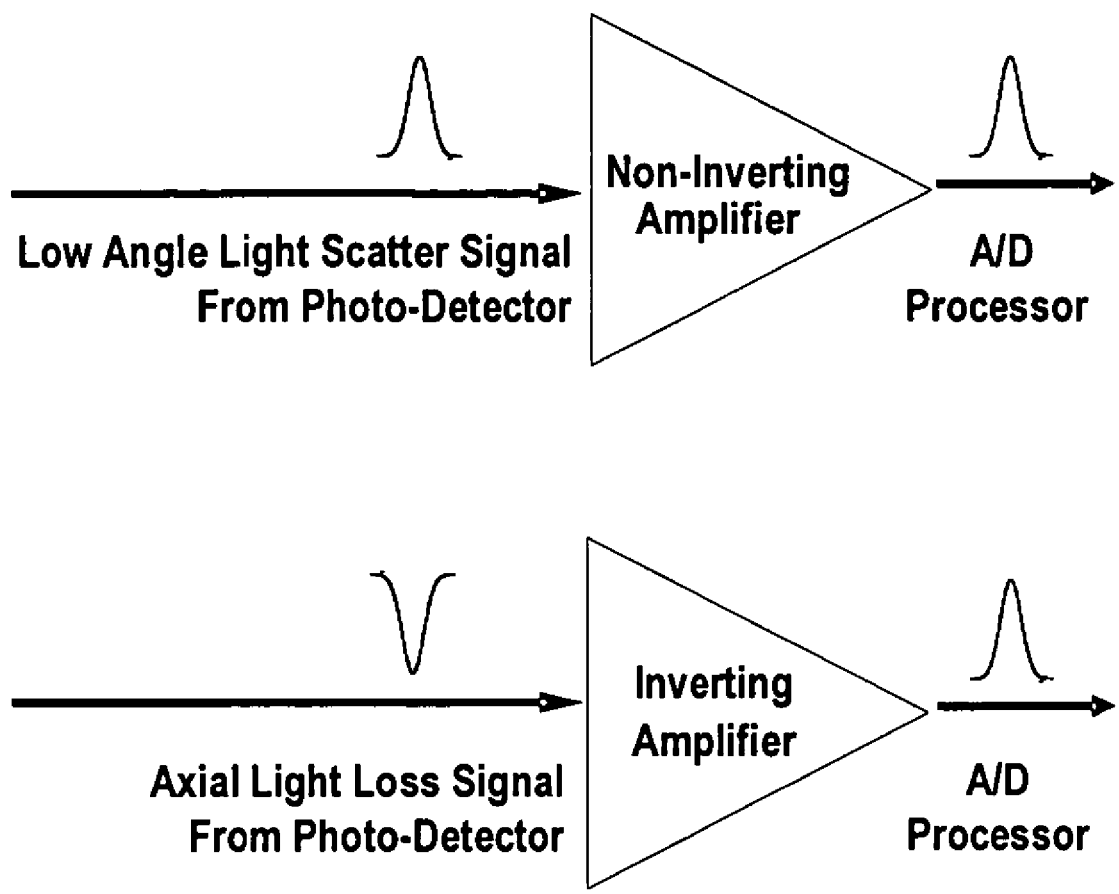
FIG. 10 is a schematic illustration of the electrical circuitries used in the optical detector assembly for processing the low angle light scatter and axial light loss signals.

Since axial light loss measurement measures the loss of energy from the beam of incident light, whereas low angle light scatter measurement measures the increase in light, different electronic circuitries are required for measuring these two different optical properties. As shown in FIG. 10, the electronic circuitry used for measuring the ALL signals uses an inverting amplifier, whereas the electronic circuitry used for measuring the low angle light scatter signals uses a non-inverting amplifier.

An optical detector assembly is used for measuring the ALL and low angle light scatter signals. Many designs of the optical detection hardware can be used for the purpose of the present invention. In one embodiment, the optical detector assembly includes two discrete photo-detectors, of appropriate size and geometry, placed on a printed circuit board (PCB). One photo-detector is used for measuring the ALL signals, and the other photo-detector is used for measuring the light scatter signals. Signals from the photo-detectors are sent to conditioning circuitry within an experimental hematology analyzer which is described hereinafter. In another embodiment, the optical detector assembly includes a planar photodiode array with sensing regions of appropriate size and geometry for measuring the ALL and light scatter signals. Signals from the photodiode array are sent to conditioning circuitry within the experimental hematology analyzer. In a further embodiment, the optical detector assembly includes a fiber optic array for measuring the ALL and light scatter signals. The suitable fiber optic array has been described in detail in U.S. Pat. No. 6,798,508, which is herein incorporated by reference in its entirety.

On the other hand, when a particle or a blood cell, suspended in a conductive solution, passes through the flow cell, an electrical signal can be measured due to impedance change. The pulse shape, height and width, are directly related to the size of a particle, and can be converted to the size of the particles measured. When two or more particles of different sizes are measured, the histogram obtained from the measurement can represent size distribution of the particles. The detection methods used for blood cell counting and sizing by a blood analyzer equipped with a DC impedance measurement device are generally described in U.S. Pat. Nos. 2,656,508, 3,810,011 and 5,125,737, which are hereby incorporated by reference in their entirety.

One reagent system suitable for lysing blood sample for the purpose of the present invention comprises an isotonic blood diluent, such as the diluents described in U.S. Pat. Nos. 4,521,518, 4,528,274, 5,935,857, and a lysing reagent, such as the lysing reagents described in U.S. Pat. Nos. 5,763,280, 5,834,315 and 6,573,102, these are hereby incorporated by reference in their entirety. Alternatively, the reagent system can also be an isotonic lysing reagent as described in U.S. Pat. No. 5,882,934 which is hereby incorporated by reference in its entirety. This reagent dilutes the blood sample and lyses the red blood cells at the same time for subsequent analysis.

Figure 1A:
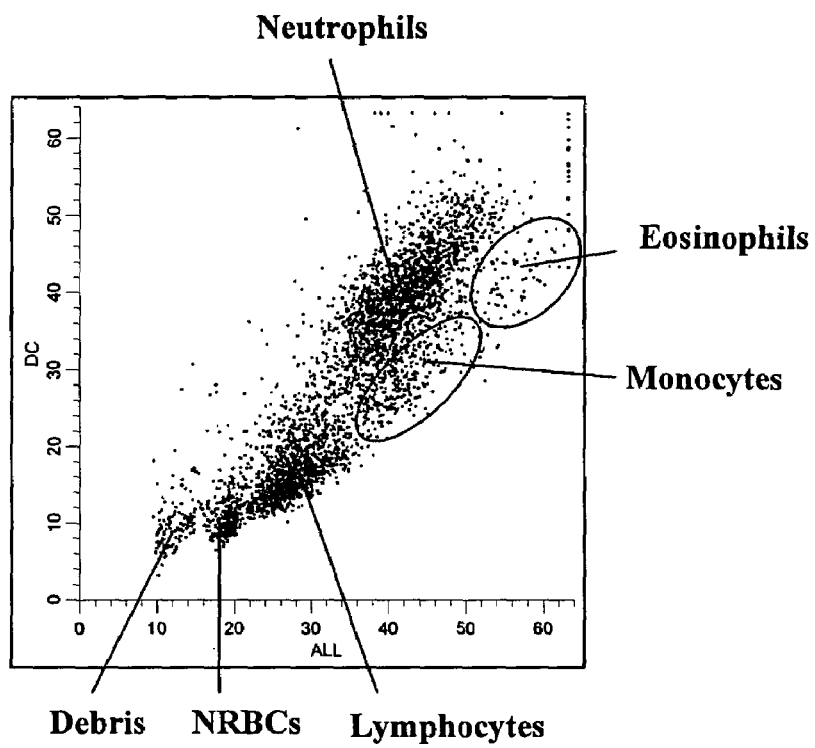
FIG. 1A is a DC vs. ALL scattergram of a clinical whole blood sample analyzed using the reagents and method described in Example 1.

Example 1 illustrates the method of differentiating nucleated red blood cells using axial light loss and DC impedance measurements. FIG. 1A shows a DC vs. ALL scattergram of a clinical whole blood sample, containing nucleated red blood cells, processed and analyzed using the reagents and the procedure described in Example 1. As shown, the nucleated red blood cells form a cluster which is separated from white blood cells and from cell debris.

Figure 1B:
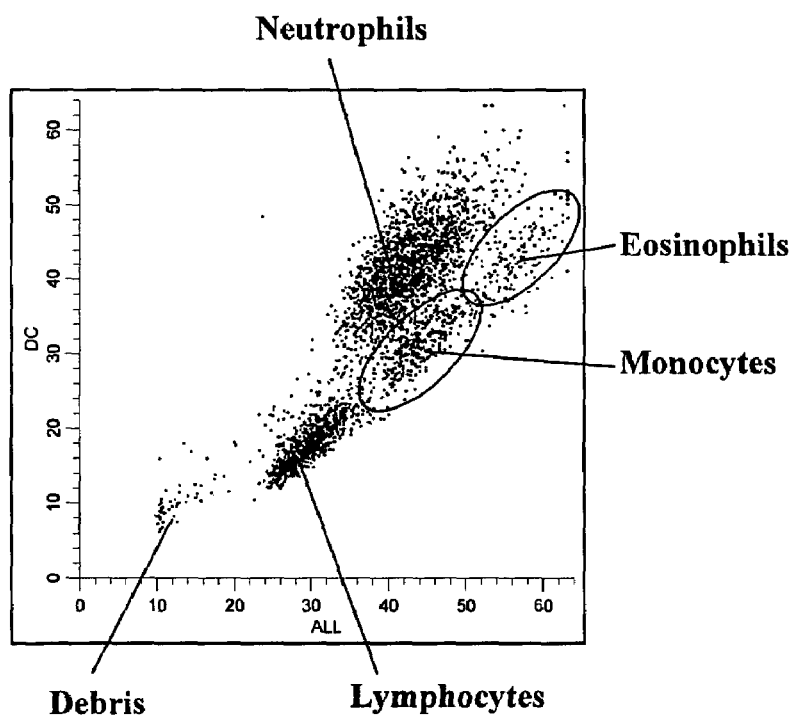
FIG. 1B is a DC vs. ALL scattergram of a normal whole blood sample analyzed using the reagents and method described in Example 1.

FIG. 1B shows a DC vs. ALL scattergram of a normal whole blood sample obtained using the reagents and the process described in Example 1. As can be readily seen, there is no cell population present in the region where nucleated red blood cells reside.

The NRBC concentration of the sample can be calculated by dividing the number of cells in the identified NRBC cluster (FIG. 1A) by the numbers of the white blood cells (WBC) and multiplying the quotient by 100. The NRBC concentration can be reported as the number of NRBC/100 WBC, which is the same as the unit of the manual reference method, or can be reported as an absolute number of NRBC per microliter ($\mu L$) of a whole blood.

Moreover, as shown in FIGS. 1A and 1B, the white blood cells are further differentiated into four subpopulations using the axial light loss and DC impedance measurements. The four subpopulations include lymphocytes, monocytes, neutrophils and eosinophils.

In another embodiment, the present invention provides a method of differentiating nucleated red blood cells from other cell types using a combination of axial light loss and a low angle light scatter measurements. In this embodiment, a lysed blood sample is analyzed in a flow cell by measuring axial light loss and low angle light scatter signals. The nucleated red blood cells are differentiated from other cell types by using the obtained axial light loss and low angle light scatter signals. Preferably, the low angle light scatter signal is measured in less than 10°, more preferably, from about 1° to about 7°, and most preferably from about 4° to about 6°.

Figure 2A:
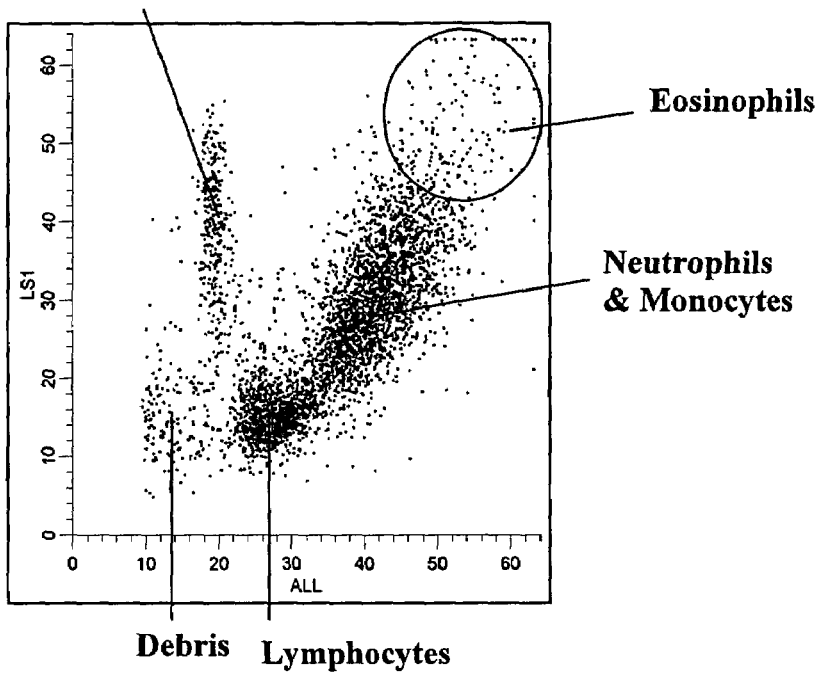
FIG. 2A is a LS1 vs. ALL scattergram of the clinical whole blood sample shown in FIG. 1A.

FIG. 2A shows a LS1 (light scatter at 5.1°) vs. ALL scattergram of the same clinical whole blood sample shown in FIG. 1A, obtained using the reagents and the process described in Example 1. As shown, the nucleated red blood cells form a cluster which is clearly separated from white blood cells and from cell debris.

Figure 2B:
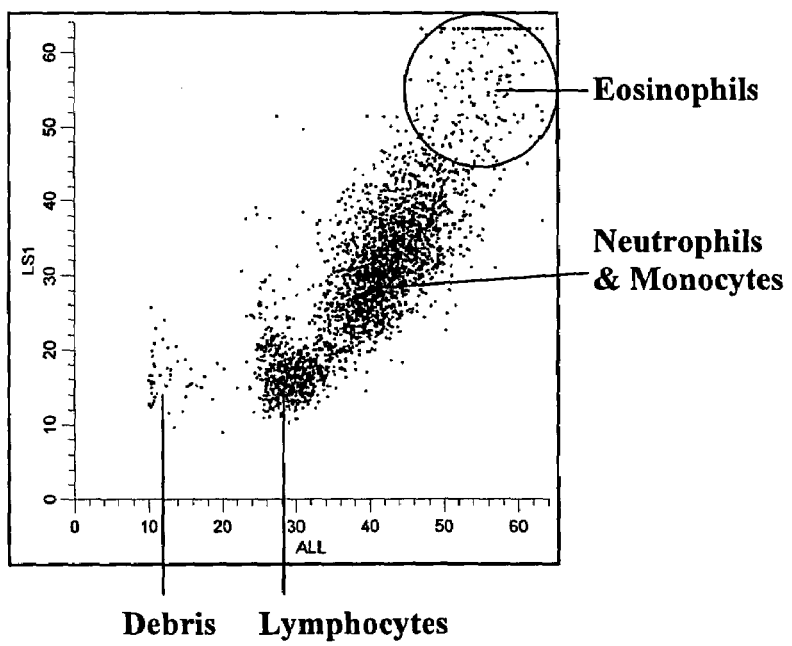
FIG. 2B is a LS1 vs. ALL scattergram of the normal whole blood sample shown in FIG. 1B.

FIG. 2B shows a LS1 vs. ALL scattergram of the same normal whole blood sample shown in FIG. 1B. Again, no cluster is present in the region where nucleated red blood cells reside.

Furthermore, as shown in FIGS. 2A and 2B, the white blood cells are further differentiated into three subpopulations using the axial light loss and the low angle light scatter measurements. The three subpopulations include lymphocytes, a sum of monocytes and neutrophils, and eosinophils.

In a further embodiment, the present invention provides a method of differentiating nucleated red blood cells from other cell types using a combination of axial light loss, low angle light scatter and DC impedance measurements. In this embodiment, a lysed blood sample is analyzed in a flow cell by measuring axial light loss, low angle light scatter and DC impedance signals. The nucleated red blood cells are differentiated from other cell types by using the obtained axial light loss, low angle light scatter and DC impedance signals. The low angle light scatter signal is measured in the same range described previously, i.e., from about 1° to about 7°, more preferably, from about 4° to about 6°.

Figure 3A:
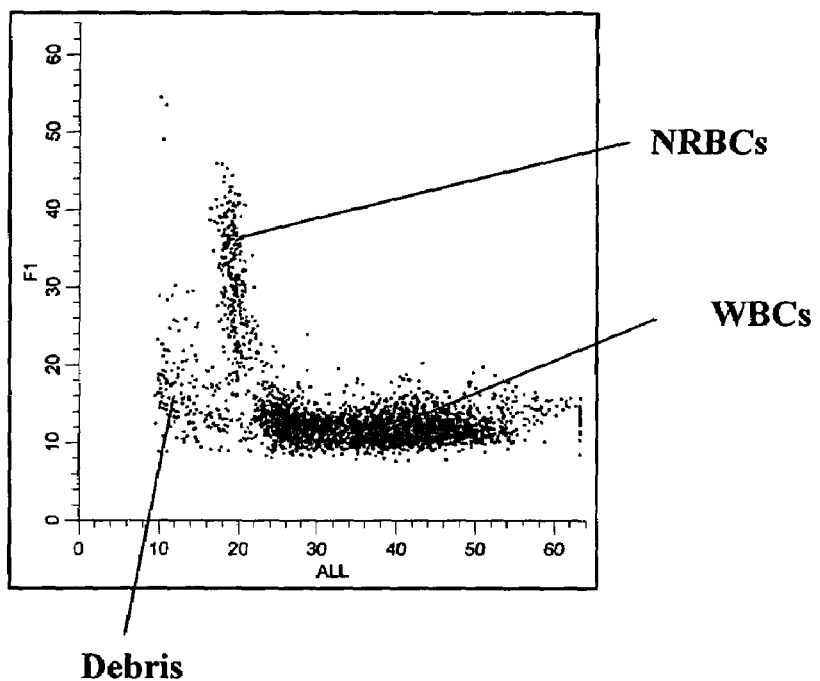
FIG. 3A is a F1 vs. ALL scattergram of the same clinical whole blood sample shown in FIG. 1A.
Figure 3B:
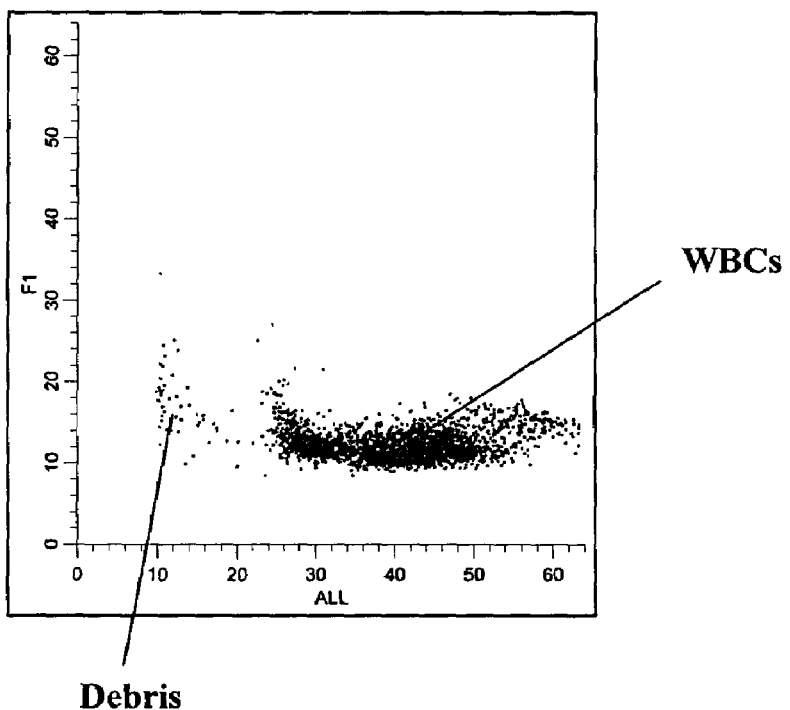
FIG. 3B is a F1 vs. ALL scattergram of the same normal whole blood sample shown in FIG. 1B.

More specifically, in one embodiment, a cell distribution scattergram was constructed by using the axial light loss signal and a function of the low angle light scatter and DC impedance signals. As one example, FIG. 3A shows a F1 vs. ALL scattergram of the same clinical whole blood sample shown in FIG. 1A, obtained using the reagents and the process described in Example 1. In this case, function F1 equals to ((DC+LS1)/DC×1000)). As shown, the nucleated red blood cells clearly separated from white blood cells and from cell debris. FIG. 3B shows a F1 vs. ALL scattergram of the same normal whole blood sample shown in FIG. 1B.

Figure 4A:
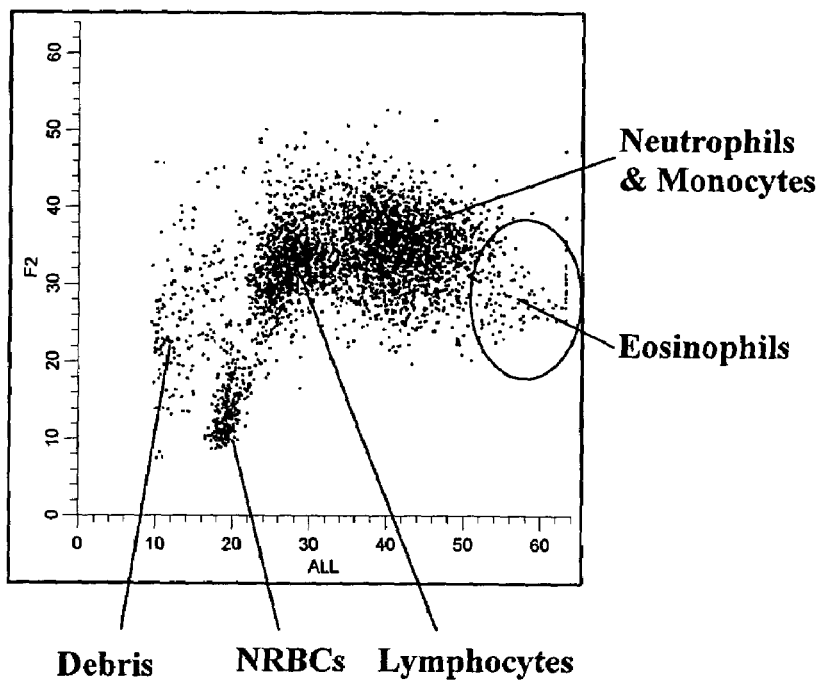
FIG. 4A is a F2 vs. ALL scattergram of the same clinical whole blood sample shown in FIG. 1A.
Figure 4B:
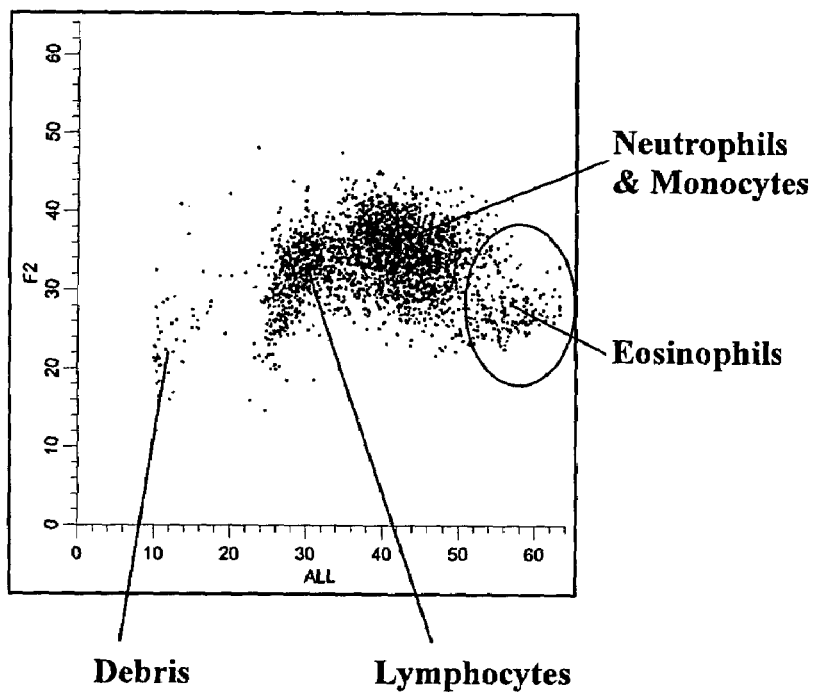
FIG. 4B is a F2 vs. ALL scattergram of the same normal whole blood sample shown in FIG. 1B.
Figure 5A:
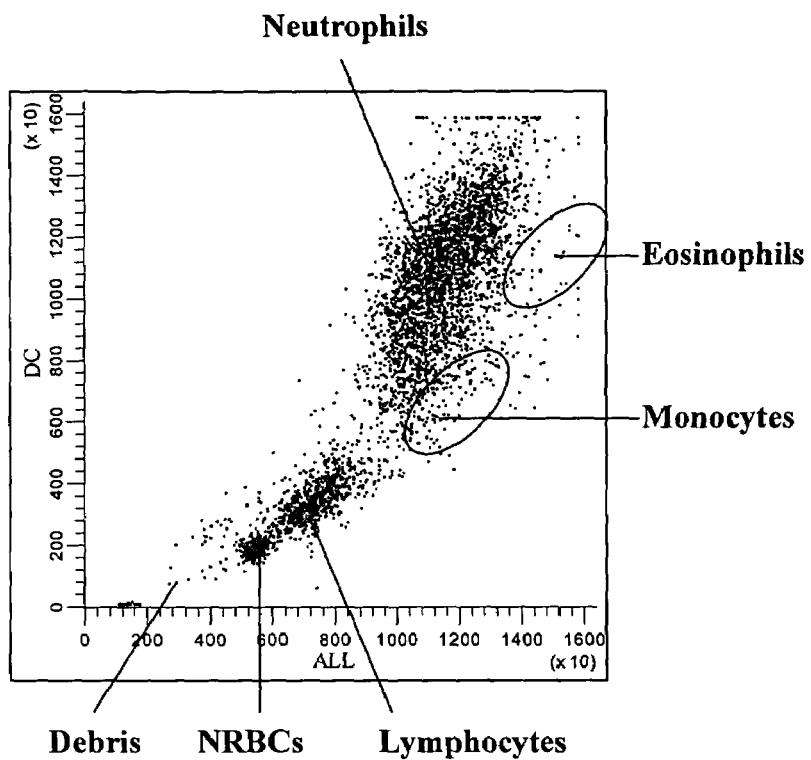
FIG. 5A is a DC vs. ALL scattergram of a clinical whole blood sample analyzed using the reagents and method described in Example 3.
Figure 5B:
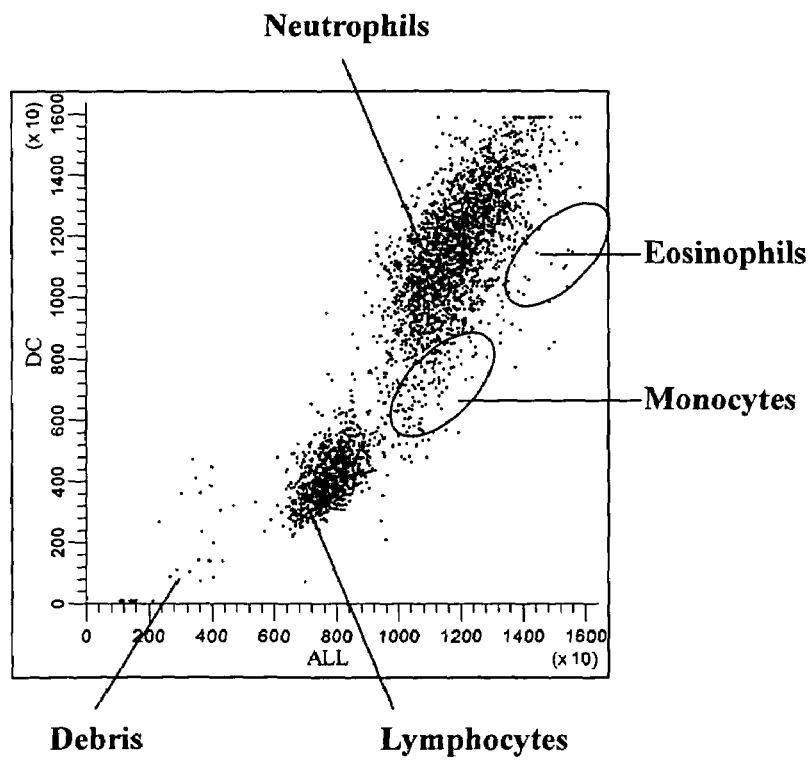
FIG. 5B is a DC vs. ALL scattergram of a normal whole blood sample analyzed using the reagents and method described in Example 3.
Figure 6A:
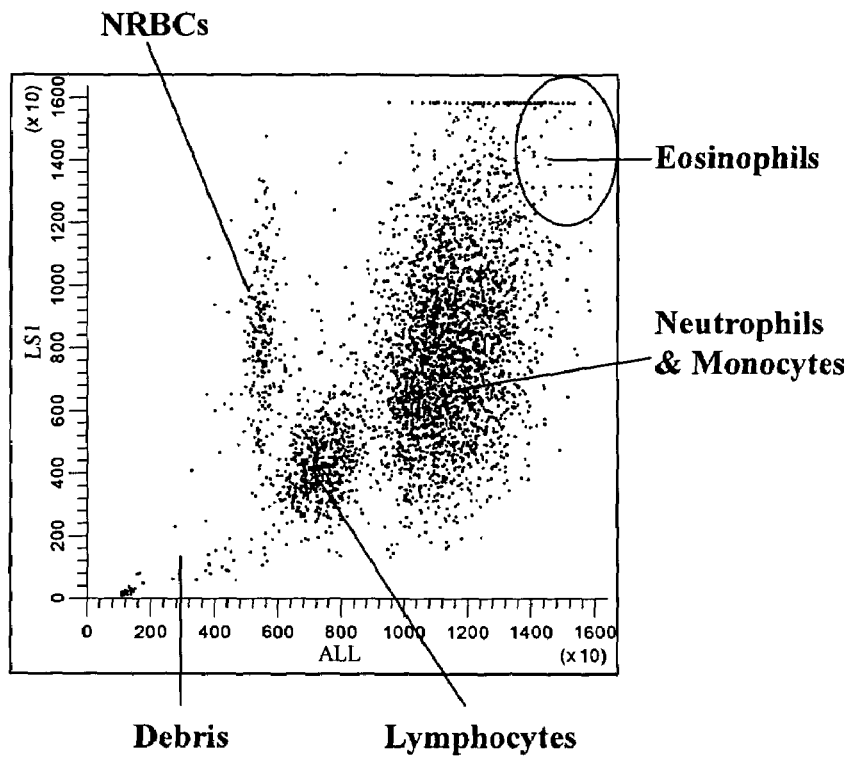
FIG. 6A is a LS1 vs. ALL scattergram of the clinical whole blood sample shown in FIG. 5A.
Figure 6B:
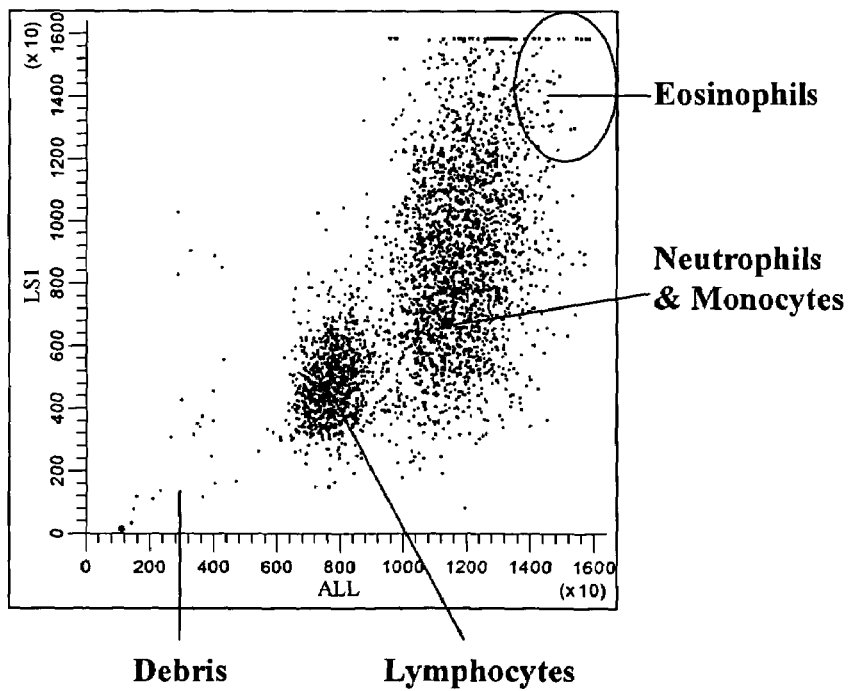
FIG. 6B is a LS1 vs. ALL scattergram of the normal whole blood sample shown in FIG. 5B.
Figure 7A:
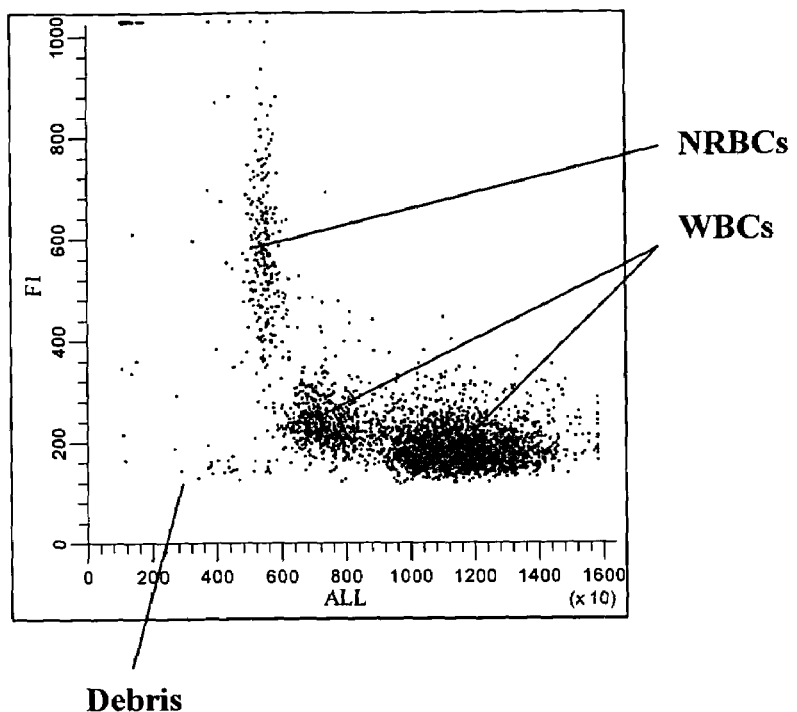
FIG. 7A is a F1 vs. ALL scattergram of the same clinical whole blood sample shown in FIG. 5A.
Figure 7B:
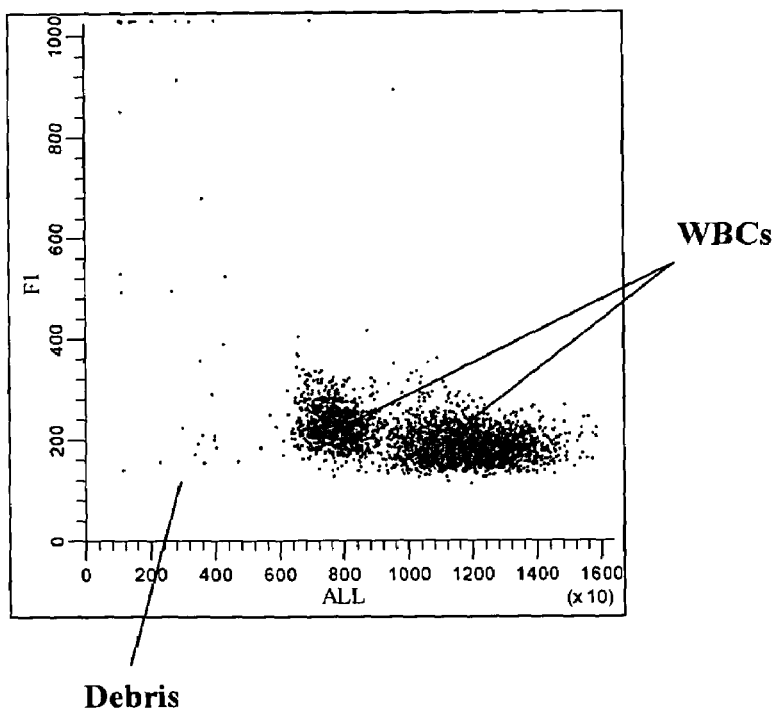
FIG. 7B is a F1 vs. ALL scattergram of the same normal whole blood sample shown in FIG. 5B.
Figure 8A:
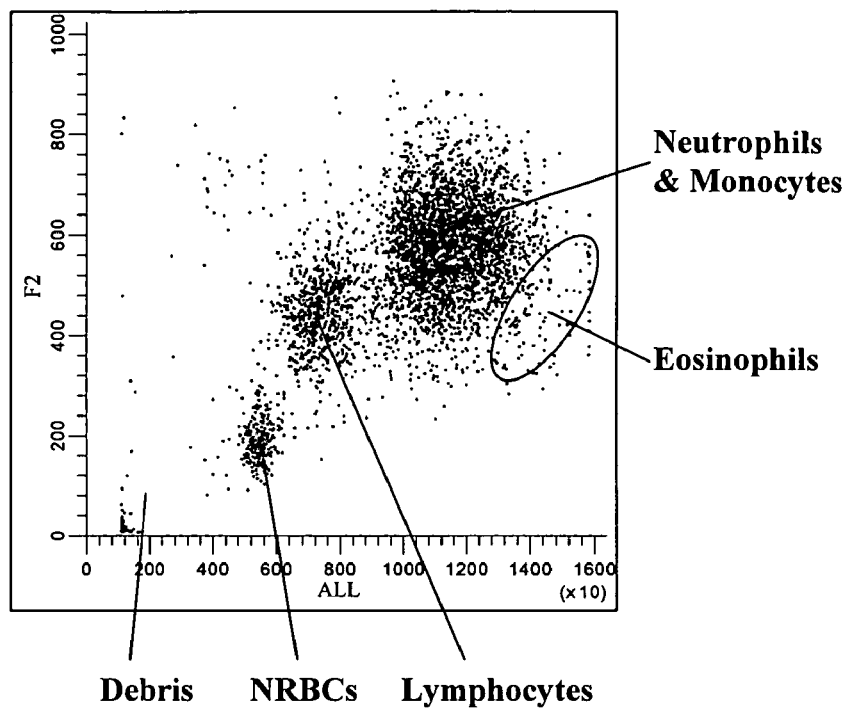
FIG. 8A is a F2 vs. ALL scattergram of the same clinical whole blood sample shown in FIG. 5A.
Figure 8B:
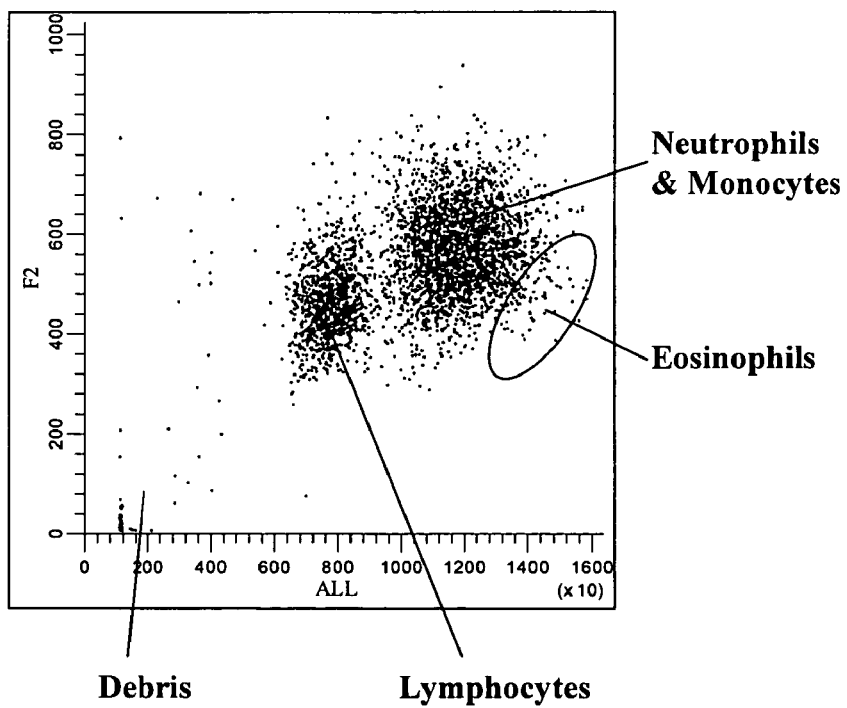
FIG. 8B is a F2 vs. ALL scattergram of the same normal whole blood sample shown in FIG. 5B.

As another example, FIG. 4A shows a F2 vs. ALL scattergram of the same clinical whole blood sample shown in FIG. 1A, obtained using the reagents and the process described in Example 1. In this case, function F2 equals to (DC/(DC+LS1)×1000)). As shown in this scattergram, the nucleated red blood cells clearly separated from white blood cells and from cell debris. FIG. 4B shows a F2 vs. ALL scattergram of the same normal whole blood sample shown in FIG. 1B.

It is apparent from the illustrations provided by FIGS. 3A and 4A that the separation of the nucleated red blood cells from other cell types was further enhanced by using the functions of DC and LS1.

Alternatively, it has been found that the separation of the nucleated red blood cells from other cell types can also be enhanced using one or more functions of DC, LS1 and ALL. Furthermore, in the previously discussed embodiments using DC and ALL, and using ALL and low angle light scatter measurements for differentiation of nucleated red blood cells, one or more functions of DC and ALL, or one or more functions of ALL and LS1 can also be utilized for further enhancing the separation of the nucleated red blood cells from other cell types.

Example 3 illustrates another example using a different reagent system and the methods of the present invention as described above to differentiate the nucleated red blood cells from other cell types. As shown in FIGS. 5A, 6A, 7A and 8A, the nucleated red blood cells clearly separate from white blood cells and from cell debris in DC vs. ALL, LS1 vs. ALL, F1 vs. ALL and F2 vs. ALL scattergrams, respectively.

As described previously, the nucleated red blood cells can overlap with other cell types, particularly white blood cells, even when they are measured by fluorescence measurement. The methods of the present invention utilize multiple parameters and functions thereof to enhance the differentiation of the nucleated red blood cells for enumeration of this specific immature red blood cell population.

Figure 9:
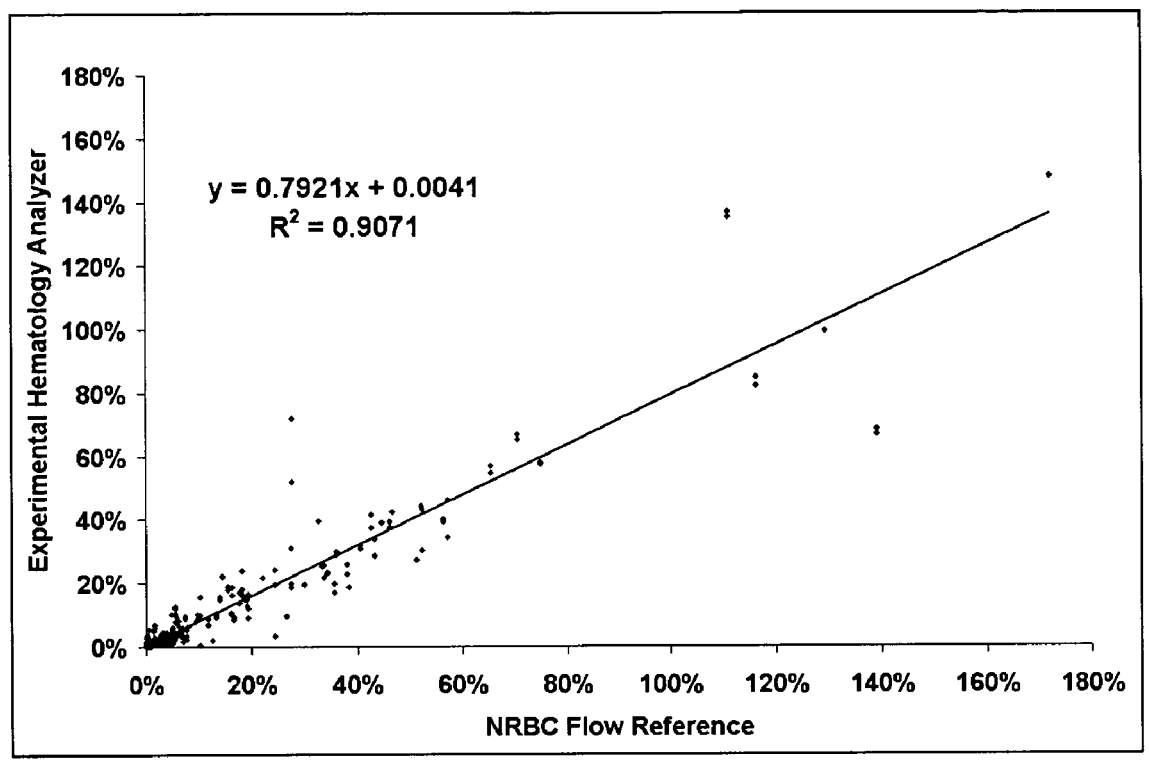
FIG. 9 is a correlation curve between results obtained by a flow cytometry reference method and the method of the present invention as described in Example 4.

As shown in FIG. 9 and described in Example 4 a total of 336 whole blood samples including 132 of clinical samples were analyzed using the process and the reagents described in Example 1. The NRBC results were obtained from the differential analysis using the F1 vs. ALL scattergram. FIG. 9 illustrates the linear correlation between the results of a flow cytometry reference method which is described hereinafter and the results obtained using the method of the present invention.

In another embodiment, the method further comprises correction of white blood cell counts. Historically, when white blood cells are counted using a direct current impedance method, the nucleated red blood cells are counted, or partially counted together with white blood cells because they are not differentiated from white blood cells. The interference caused by nucleated red blood cells can result in elevated and erroneous white blood cell counts. Traditionally, the WBC count is corrected manually by subtracting the numbers of the nucleated red blood cells obtained by manual differential method from the WBC count reported from the instrument. With the method of the present invention, the contribution of this population to the white blood cell count can be corrected automatically. More specifically, a total count of the remaining blood cells in the sample mixture can be further obtained during the analysis of the sample mixture using the measurements described above, with the apparatus described hereinafter. It is noted that the remaining blood cells in the sample mixture above the detection threshold are mainly the nucleated blood cells including white blood cells and nucleated red blood cells if present, and potentially a small amount of cell debris. Upon differentiating the nucleated red blood cells and cell debris from the white blood cells as described above, a corrected white blood cell count can be obtained by subtracting the nucleated red blood cells and cell debris from a total count of the remaining blood cells. The corrected WBC can be reported automatically by the hematology analyzer, and no further manual correction is required from the laboratory personnel.

The apparatus which enables the methods described above for differentiation of nucleated blood cells includes (a) a focused-flow flow cell including inlet and outlet means for the ingress and egress of a sample mixture; (b) introducing means for introducing a blood cell sample including nucleated blood cells into the flow cell inlet to cause the nucleated blood cells to flow through the flow cell; (c) a beam of incident light arranged such that the axis of its light rays pass through the flow cell at right angles to the flow of the nucleated blood cells; (d) an optical detector assembly enabling detection of axial light loss and low angle light scatter signals at various angles less than 10° to the axis of the incident light; and (e) a DC impedance detector for measuring impedance signals as cells pass through the aperture of the flow cell.

As described previously, the optical detector assembly enabling detection of axial light loss and low angle light scatter signals can have several hardware designs. In the experimental hematology analyzer used in the Examples described hereinafter, the optical detector assembly has two discrete photo-detectors, one for measurement of axial light loss signals and the other for measurement of low angle light scatter signals.

In a preferred embodiment, the flow cell can be a square shape flow cell with dimensions in a range from 30 to 250 μm, which enables measurement of axial light loss signals, low angle light scatter signals and detection of DC impedance signals. More preferably, the flow cell is a 50 μm square shape flow cell. Preferably, the light scatter signals in the range from about 1° to about 7° are detected. More preferably, the light scatter signals from about 4° to about 6° are detected. The DC impedance detector is described in details in U.S. Pat. No. 5,125,737, which is herein incorporated by reference in its entirety.

Moreover, the apparatus further includes a positive displacement pump which delivers the sample mixture through the flow cell quantitatively. Therefore, a quantitative cell count of the sample mixture can be obtained.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

14 μL of an anticoagulated whole blood sample, also referred to as peripheral blood, was diluted by 614 μL of an isotonic blood diluent, Isoton® 3E (product of Beckman Coulter, Inc. Miami, Fla.), and mixed with 125 μL of a lytic reagent in a mixing chamber on an experimental hematology analyzer. About nine seconds after the addition of the lytic reagent the sample mixture was delivered to a flow cell with a sheath fluid, Isoton® 3E, for differential analysis of nucleated red blood cells. The lytic reagent was an aqueous solution containing active components for lysing red blood cells and analysis of nucleated red blood cells: 36 g/L dodecyltrimethylammonium chloride (50% solution), 3.6 g/L tetradecyl-trimethylammonium bromide, and has a pH about 4.

An experimental hematology analyzer was equipped with a detection system for detecting DC impedance, low angle light scatter and axial light loss signals generated when a cell in the sample mixture passed through the flow cell. The detection system included a DC impedance detector and an optical detector assembly as described above. The optical detector assembly enabled detection of light scatter signals at various low angles less than 10° from the incident light, including 1.9°±0.5°, 3.0°±0.5°, 3.7°±0.5°, 5.1°±0.5°, 6.0°±0.5° and 7.0°±0.5°, and axial light loss (0° to 0.5°). More specifically, the low angle light scatter signals at 5.1°±0.5° and the axial light loss (0° to 0.5°) were used for differentiating NRBC from other cell types in the instant invention, which were referred to as LS1 and ALL in the scattergrams, respectively. Using the detection system, the DC impedance, low angle light scatter and axial light loss signals could be detected together, or one or two of them could be detected selectively. Each blood cell was measured, as it passed through a 50 μm flow cell, by the detection system. The data was acquired with a 12 bit analog to digital converter (ADC) resolution.

FIG. 1A shows a DC vs. ALL scattergram obtained from a clinical blood sample, which shows a cluster of NRBC population distinguished from white blood cells and cell debris. The NRBC concentration of the analyzed sample is calculated by dividing the number of identified nucleated red blood cells by the white blood cells (WBC) and multiplying the quotient by 100. The NRBC concentration is reported as number of NRBC/100 WBC, which is the same as the unit of the manual reference method. For this sample, the result obtained using the above-described process was 7.8%, which was consistent with the reference method.

FIG. 2A shows a LS1 vs. ALL scattergram obtained from the same clinical whole blood sample shown in FIG. 1A, using the process described above. As shown in this scattergram, the nucleated red blood cells also formed a cluster which was clearly separated from white blood cells and from cell debris.

EXAMPLE 2

A fresh normal whole blood sample was analyzed using the same reagents and procedure described in Example 1. FIG. 1B shows an obtained DC vs. ALL scattergram of a normal blood sample. As shown, no cell population was present in the region where nucleated red blood cells reside.

Furthermore, as shown in FIGS. 1A and 1B the white blood cells were further differentiated into four subpopulations, i.e., lymphocytes, monocytes, neutrophils and eosinophils.

FIG. 2B shows an obtained LS1 vs. ALL scattergram of the same normal whole blood sample shown in FIG. 1B. Again, no cluster was present in the region where nucleated red blood cells reside.

Also, as shown in FIGS. 2A and 2B the white blood cells were further differentiated into three subpopulations, i.e., lymphocytes, a sum of monocytes and neutrophils, and eosinophils.

EXAMPLE 3

A clinical whole blood sample containing nucleated red blood cells and a fresh normal whole blood sample were analyzed using the process described in Example 1 on another experimental hematology analyzer which was equipped with a detection system equivalent to that described in Example 1, but the data was acquired with a 14-bit ADC resolution. The lytic reagent and the diluent used were Lyse S® 4 and Isoton® 4 (products of Beckman Coulter, Inc. Miami, Fla.).

FIGS. 5A thru 8B show the obtained scattergrams. As shown in FIGS. 5A, 6A, 7A and 8A, the nucleated red blood cells in the clinical sample clearly separate from white blood cells and from cell debris in DC vs. ALL, LS1 vs. ALL, F1 vs. ALL and F2 vs. ALL scattergrams, respectively. As shown in FIGS. 5B, 6B, 7B and 8B obtained from the normal blood sample, no cell population was present in the region where nucleated red blood cells reside. It is noted that the axis scales of the scattergrams in FIGS. 5A thru 8B are different from those shown in FIGS. 1A thru 4B because of the difference in resolution. However, the relative positions among different populations maintain the same.

EXAMPLE 4

Total of 336 whole blood samples including 132 of clinical samples were analyzed using the process and the reagents described in Example 1. The NRBC results were obtained from the differential analysis using the F1 vs. ALL scattergram. As described previously, F1 is a function of DC and LS1, which equals to ((DC+LS1)/DC×1000)).

Reference NRBC values were obtained using a manual reference method and a flow cytometric method. Using the manual NRBC reference method, 200 WBC were counted on each sample's blood smear stained with Wright stain, and the number of NRBC present in the same region were counted and divided by two. The value is reported as NRBC/100 WBC. The flow cytometric method is described in New Rapid Flow Cytometric Method for the Enumeration of Nucleated Red Blood Cells, Cytometry 37: 291–301, 1999, which is herein incorporated by reference in its entirety. FIG. 9 shows a good correlation between the NRBC results obtained using the method of the present invention and the flow cytometry reference method.

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method for differentiating nucleated red blood cells in a blood cell sample comprising the steps of;
   (a) exposing said blood cell sample to a reagent system to lyse mature red blood cells and to form a sample mixture;
   (b) analyzing said sample mixture in a flow cell by measuring axial light loss signals and DC impedance signals;
   (c) differentiating nucleated red blood cells from other cell types using signals consisting of said axial light loss and DC impedance signals obtained in step (b); and
   (d) reporting nucleated red blood cells in said blood cell sample.

2. The method of claim 1, wherein said differentiating nucleated red blood cells from other cell types uses one or more functions of said axial light loss and DC impedance signals.

3. The method of claim 1 further comprising differentiating and reporting white blood cell subpopulations.

4. The method of claim 3, wherein said white blood cell subpopulations comprise lymphocytes, monocytes, neutrophils, and eosinophils.

5. The method of claim 1, wherein reporting of said nucleated red blood cells is in the form of reporting the number of nucleated red blood cells per one hundred white blood cells, or an absolute number of nucleated red blood cells per unit volume of said blood cell sample.

6. The method of claim 5, wherein said blood cell sample includes peripheral blood, umbilical cord blood, and bone marrow of a human, and peripheral blood, umbilical cord blood, and bone marrow of a non-human.

7. The method of claim 1 further comprising the steps of: obtaining a count of remaining blood cells of said sample mixture in step (b); subtracting nucleated red blood cells and cell debris from said count of remaining blood cells to obtain a corrected white blood cell count; and reporting said corrected white blood cell count in said blood sample.

8. A method for differentiating nucleated red blood cells in a blood cell sample comprising the steps of:
   (a) exposing said blood cell sample to a reagent system to lyse mature red blood cells and to form a sample mixture;
   (b) analyzing said sample mixture in a flow cell by measuring low angle light scaler signals and an axial light loss signals;
   (c) differentiating nucleated red blood cells from other cell types using signals consisting of said low angle light scaler and axial light loss signals obtained in step (b); and
   (d) reporting nucleated red blood cells in said blood cell sample.

9. The method of claim 8, wherein said low angle light scatter signals are measured less than 10°.

10. The method of claim 9, wherein said low angle light scatter signals are measured in a range from about 1° to about 7°.

11. The method of claim 10, wherein said differentiating nucleated red blood cells from other cell types uses one or more functions of said low angle light scatter and axial light loss signals.

12. The method of claim 8, wherein reporting of said nucleated red blood cells is in the form of reporting the number of nucleated red blood cells per one hundred white blood cells, or an absolute number of nucleated red blood cells per unit volume of said blood cell sample.

13. The method of claim 12, wherein said blood cell sample includes peripheral blood, umbilical cord blood, and bone marrow of a human, and peripheral blood, umbilical cord blood, and bone marrow of a non-human.

14. The method of claim 8 further comprising differentiating and reporting white blood cell subpopulations.

15. The method of claim 14, wherein said white blood cell subpopulations comprise lymphocytes, a sum of monocytes and neutrophils, and eosinophils.

16. The method of claim 8 further comprising the steps of: obtaining a count of remaining blood cells of said sample mixture in step (b); subtracting nucleated red blood cells and cell debris from said count of remaining blood cells to obtain a corrected white blood cell count; and reporting said corrected white blood cell count in said blood sample.

17. A method for differentiating nucleated red blood cells in a blood cell sample comprising the steps of:
   (a) exposing said blood cell sample to a reagent system to lyse mature red blood cells and to form a sample mixture;
   (b) analyzing said sample mixture in a flow cell by measuring DC impedance signals, low angle light scatter signals and axial light loss signals;
   (c) differentiating nucleated red blood cells from other cell types using signals consisting of said DC impedance, low angle light scatter and axial light loss signals obtained in step (b); and
   (d) reporting nucleated red blood cells in said blood cell sample.

18. The method of claim 17, wherein said low angle light scatter signals are measured less than 10°.

19. The method of claim 18, wherein said low angle light scatter signals are measured in a range from about 1° to about 7°.

20. The method of claim 19, wherein said differentiating nucleated red blood cells from other cell types uses said axial light loss signals and one or more functions of said DC impedance and low angle light scatter signals.

21. The method of claim 19, wherein said differentiating nucleated red blood cells from other cell types uses one or more functions of said DC impedance, low angle light scatter and axial light loss signals.

22. The method of claim 17, wherein reporting of said nucleated red blood cells is in the form of reporting the number of nucleated red blood cells per one hundred white blood cells, or an absolute number of nucleated red blood cells per unit volume of said blood cell sample.

23. The method of claim 22, wherein said blood cell sample includes peripheral blood, umbilical card blood, and bone marrow of a human, and peripheral blood, umbilical cord blood, and bone marrow of a non-human.

24. The method of claim 17 further comprising differentiating and reporting white blood cell subpopulations.

25. The method of claim 24, wherein said white blood cell subpopulations comprise lymphocytes, monocytes and neutrophils, and eosinophils.

26. The method of claim 17 further comprising the steps of: obtaining a count of remaining blood cells of said sample mixture in step (b); subtracting nucleated red blood cells and cell debris from said count of remaining blood cells to obtain a corrected white blood cell count; and reporting said corrected white blood cell count in said blood sample.

* * * * *